United States Patent
Dagle et al.

(10) Patent No.: US 10,647,625 B2
(45) Date of Patent: May 12, 2020

(54) SINGLE STEP CONVERSION OF ETHANOL TO BUTADIENE

(71) Applicant: BATTELLE MEMORIAL INSTITUTE, Richland, WA (US)

(72) Inventors: Vanessa Dagle, Richland, WA (US); Robert A. Dagle, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 15/837,382

(22) Filed: Dec. 11, 2017

(65) Prior Publication Data

US 2018/0222813 A1    Aug. 9, 2018

Related U.S. Application Data

(60) Provisional application No. 62/455,768, filed on Feb. 7, 2017.

(51) Int. Cl.
*C07C 1/24*  (2006.01)
*C07C 1/20*  (2006.01)

(52) U.S. Cl.
CPC .............. *C07C 1/24* (2013.01); *C07C 1/20* (2013.01); *C07C 2521/06* (2013.01); *C07C 2521/08* (2013.01); *C07C 2523/42* (2013.01); *C07C 2523/46* (2013.01); *C07C 2523/50* (2013.01)

(58) Field of Classification Search
None
See application file for complete search history.

(56) References Cited

U.S. PATENT DOCUMENTS

| | | | | |
|---|---|---|---|---|
| 2016/0082417 A1* | 3/2016 | Lewandowski | ........... | C07C 1/20 585/607 |
| 2017/0349503 A1* | 12/2017 | Chinta | ........... | B01J 23/36 |
| 2018/0104671 A1* | 4/2018 | Sae-Khow | ........... | C07C 1/20 |
| 2018/0208522 A1* | 7/2018 | Cadran | ........... | B01J 37/06 |

FOREIGN PATENT DOCUMENTS

| | | | |
|---|---|---|---|
| WO | 2012015340 A1 | 2/2012 | |
| WO | 2014129248 A1 | 8/2014 | |
| WO | WO-2014129248 A1 * | 8/2014 | ............. B01J 23/14 |

(Continued)

OTHER PUBLICATIONS

Jones et al. "Investigations into the conversion of ethanol into 1,3-butadiene", Catal. Sci. Technol., 2011, 1, 267-272. (Year: 2011).*

(Continued)

*Primary Examiner* — Ali Z Fadhel
(74) *Attorney, Agent, or Firm* — Derek H. Maughan

(57) ABSTRACT

A process for producing 1,3-butadiene (BD) from ethanol in a single step by s7passing a mixture containing ethanol in a gas phase over a multifunctional catalyst having a transition metal dispersion of at least 30% on a silica metal oxide support. In some examples the multifunctional catalyst comprises a silica metal oxide having a surface area of at least 200 m^2/g. The multifunctional catalyst can include a transition metal oxide, a silica metal oxide made from a high purity silica gel, mesoporous silica and fumed silica, such as high purity SBA16, SBA15, or Davisil grade 646.

12 Claims, 20 Drawing Sheets

| ZrO$_2$ loading (wt%) | Lewis acid sites concentration (µmoles/g) | Conversion (%) | Selectivities (%) | | | | | | | | | |
|---|---|---|---|---|---|---|---|---|---|---|---|---|
| | | | BD | C$_2$= | C$_3$= | C$_4$= | DEE | Ethyl Acetate | Butanol | Acetaldehyde | Crotonaldehyde | Others* |
| 1 | 17.3 | 78.6 | 71.2 | 4.1 | 1.0 | 2.4 | 1.3 | 1.4 | 0.8 | 14.2 | 1.1 | 2.5 |
| 2 | 19.2 | 80.6 | 69.8 | 5.1 | 1.0 | 4.1 | 2.1 | 2.1 | 1.4 | 10.7 | 0.9 | 2.8 |
| 4 | 26.0 | 85.9 | 69.1 | 3.7 | 1.2 | 5.5 | 1.6 | 2.9 | 1.8 | 9.2 | 0.7 | 4.3 |
| 10 | 28.4 | 82.3 | 62.4 | 8.4 | 1.3 | 5.7 | 2.5 | 3.1 | 1.7 | 9.3 | 0.8 | 4.8 |

T= 325°C, WHSV = 0.45 hr$^{-1}$, P= 1 atmosphere, 24.3% ethanol in N$_2$, SiO$_2$= Davisil 646
*Others= C$_5$ olefins, C$_2$-C$_5$ alkanes, acetic acid, acetone, butanone, pentanone, CO$_2$. Acid sites determined after pyridine desorption at 150°C.
BD= Butadiene, DEE= Diethylether

(56) References Cited

FOREIGN PATENT DOCUMENTS

WO      WO-2018182450 A1 * 10/2018  .............. B01J 21/06

OTHER PUBLICATIONS

Jones et al. Supporing Information, "Investigations into the conversion of ethanol into 1,3-butadiene", Catal. Sci. Technol., 2011, 1, 267-272. (Year: 2011).*
Sushkevich et al. "Design of a Metal-Promoted Oxide Catalyst for the Selective Synthesis of Butadiene from Ethanol", ChemSusChem 2014, 7, 2527-2536. (Year: 2014).*
Sun et al. "Catalysis Chemistry of Dimethyl Ether Synthesis", ACS Catal. 2014, 4, 3346-3356. (Year: 2014).*
Davisil Brochure, copywrights 2016.*
Angelici, C., et al., Chemocatalytic Conversion of Ethanol into Butadiene and Other Bulk Chemicals, ChemSusChem Reviews, 6, 2013, 1595-1614.
Baerdemaeker, T. D., et al., Bimetallic Zn and Hf on Silica Catalysts for the Conversion of Ethanol to 1,3-Butadiene, ACS Catalysis, 5, 2015, 3393-3397.
Egloff, G., et al., Conversion of oxygen derivates of Hydrocarbon into Butadiene, Chem. Rev., 36, 1945, 63-141.
Emeis, C. A., Determination of Integrated Molar Extinction Coefficients for Infrared Absorption Bands of Pyridine Adsorbed on Solid Acid Catalysts, Journal of Catalysis, 141, 1993, 347-354.
Ezinkwo, G. O., et al., Fundamental Issues of Catalytic Conversion of Bio-Ethanol into Butadiene, ChemBioEng Rev, 1, 5, 2014 194-203.
Golay, S., et al., Influence of the catalyst acid/base properties on the catalytic ethanol dehydration under steady state and dynamic conditions. In situ surface and gas-phase analysis, Chemical Engineering Science, 54, 1999, 3593-3598.
Janssens, W., et al., Ternary Ag/MgO—SiO2 Catalysts for the Conversion of Ethanol into Butadiene, ChemSusChem, 8, 2015, 994-1008.
Jones, H. E., et al., Butadiene from Ethanol, Reaction Mechanism, Journal of the American Chemical Society, 71, 1949, 1822-1828.
Jones, M. D., et al., Investigations into the conversion of ethanol into 1,3-butadiene, Catal. Sci. Technol., 1, 2011, 267-272.
Jones, M. D., Catalytic transformation of ethanol into 1,3-butadiene, Chemistry Central Journal, 3, 53, 2014, 1-5.
Onfroy, T., et al., Development of the acidity of zirconia-supported niobia catalysts, Catalysis Letters, 89, 1-2, 2003, 15-19.
Patel, A. D., et al., Sustainability assessment of novel chemical processes at early stage: application to biobased processes, Energy & Environmental Science, 5, 2012, 8340-8444.
Patel, A. D., et al., Early-Stage Comparative Sustainability Assessment of New Bio-based Processes, ChemSusChem, 6, 2013, 1724-1736.
Plotkin, J. S., The Continuing Quest for Butadiene, American Chemical Society, 2016, 1-3.
Sun, J., et al., Recent Advances in Catalytic Conversion of Ethanol to Chemicals, ACS Catalysis, 4, 2014, 1078-1090.
Sushkevich, V. L., et al., Mechanistic Study of Ethanol Dehydrogenation over Silica-Supported Silver, ChemCatChem, 5, 2013, 2367-2373.
Sushkevich, V. L., et al., Meerwein-Ponndorf-Verley-Oppenauer reaction of crotonaldehyde with ethanol over Zr-containing catalysts, Journal of Catalysis, 315, 2014, 121-129.
Sushkevich, V. L., et al., Mechanistic study of ethanol conversion into butadiene over silver promoted zirconia catalysts, Applied Catalysis B: Environmental, 215, 2017, 36-49.
Varsisli, D., et al., Ethylene and diethyl-ether production by dehydration reaction of ethanol over different heteropolyacid catalysts, Chemical Engineering Science, 62, 2007, 5349-5352.
White, W. D., Butadiene production process overview, Chemico-Biological Interactions, 166, 2007, 10-14.
Zaki, T., Catalytic dehydration of ethanol using transition metal oxide catalysts, Journal of Colloid and Interface Science, 284, 2005, 606-613.
Makshina, E. V., et al., Review of old chemistry and new catalytic advances in the on-purpose synthesis of butadiene, Chem. Soc. Rev., 43, 2014, 7917-7953.
Sushkevich, V. L., et al., Design of a Metal-Promoted Oxide Catalyst for the Selective Synthesis of Butadiene from Ethanol, ChemSusChem, 7, 2014, 2527-2536.
International Search Report and Written Opinion of the International Searching Authority for International Application No. PCT/US2017/066024, International Filing Date Dec. 13, 2017, dated Feb. 28, 2018.
Sushkevich, V. L., et al., Ethanol conversion into butadiene over Zr-containing molecular sieves doped with silver, Green Chemistry, 17, 2015, 2552-2559.

* cited by examiner

| Catalyst | Temperature (°C) | WHSV (hr-1) | Conversion (%) | Selectivity (%) | | | | | | | | | BD yield | Prod*** |
|---|---|---|---|---|---|---|---|---|---|---|---|---|---|---|
| | | | | Butadiene (BD) | C₂= | C₃= | C₄= | DEE | EA | BuOH | HAC | others | | |
| 4Ag/4ZrO₂/SiO₂-SBA-16* | 325 | 0.68 | 94.9 | 70.9 | 4.5 | 1.9 | 9.9 | 2.4 | 0.7 | 0.4 | 4.7 | 4.6 | 67.3 | 0.27 |
| 4Ag/4ZrO₂/HPSiO₂ Silica gel davisil 646** | 325 | 0.47 | 89.2 | 73.6 | 5.5 | 1.5 | 5.2 | 3.0 | 1.0 | 0.8 | 6.7 | 2.7 | 61.5 | 0.17 |
| 2Ag/4ZrO₂/SiO₂** | 320 | 0.3 | 55.2 | 71.3 | 2.0 | 3.0 | 3.0 | 2.4 | 1.6 | 1.0 | 0 | 15.7 | 39.4 | 0.07 |

*T = 325°C, P = 1 atmosphere, 24.3% EtOH in N₂
**T = 325°C, P = 1 atmosphere, 50% EtOH in N₂
***Productivity= grams of butadiene per gram of catalyst and per hour

Fig. 3

| SiO₂ support | WHSV (hr⁻¹) | Conv (%) | Selectivities (%) | | | | | | | | | | Butadiene yield (%) | Productivity$^c$ |
|---|---|---|---|---|---|---|---|---|---|---|---|---|---|---|
| | | | BD | C$_2$⁼ | C$_3$⁼ | C$_4$⁼ | DEE$^a$ | Ethyl Acetate | Butanol | Acetaldehyde | Crotonaldehyde | Others$^b$ | | |
| Davisil 636 | 0.23 | 82.7 | 65.2 | 7.3 | 1.9 | 14.1 | 2.5 | 1.2 | 1.2 | 3.8 | 0.2 | 2.6 | 51.4 | 0.07 |
| Large pores Alfa Aesar | 0.23 | 48.7 | 29.3 | 48.7 | 1.1 | 3.7 | 9.9 | 0.5 | 0.4 | 4.5 | 0.2 | 1.7 | 14.3 | 0.02 |
| | 0.11 | 81.3 | 36.7 | 41.4 | 1.6 | 2.3 | 7.7 | 0.3 | 0.4 | 2.8 | 0.0 | 6.8 | 29.8 | 0.02 |
| Davisil 646 | 0.23 | 76.1 | 75.3 | 3.3 | 1.4 | 4.9 | 1.6 | 2.1 | 1.9 | 5.9 | 0.3 | 3.3 | 57.3 | 0.08 |
| Davisil 645 | 0.23 | 29.5 | 41.6 | 15.9 | 1.2 | 3.7 | 4.7 | 0.6 | 3.8 | 12.4 | 0.5 | 15.6 | 12.3 | 0.02 |
| | 0.07 | 82.0 | 75.1 | 3.4 | 1.8 | 8.5 | 1.6 | 1.8 | 1.6 | 3.4 | 0.8 | 4.0 | 61.6 | 0.03 |
| after ion-exchange | 0.23 | 79.6 | 73.4 | 5.3 | 1.7 | 5.1 | 1.8 | 1.8 | 1.4 | 5.0 | 0.7 | 3.8 | 58.4 | 0.08 |
| Davisil 923 | 0.23 | 84.8 | 56.8 | 20.2 | 1.9 | 6.4 | 5.9 | 1.1 | 0.7 | 4.2 | 0.2 | 2.6 | 48.2 | 0.07 |
| KSKG-GOST 3956-76 | 0.23 | 84.7 | 78.3 | 1.8 | 1.5 | 4.2 | 0.7 | 1.0 | 2.2 | 5.9 | 0.8 | 3.6 | 66.3 | 0.09 |
| KSMG-GOST 3956-76 | 0.23 | 100.0 | 0.0 | 97.9 | 0.2 | 0.9 | 0.0 | 0.0 | 0.0 | 0.7 | 0.0 | 0.3 | 0 | 0 |
| Fumed silica cab-o-sil EL90 | 0.23 | 37.1 | 39.2 | 22.0 | 1.0 | 3.4 | 10.0 | 1.4 | 0.4 | 12.2 | 0.3 | 10.1 | 14.5 | 0.02 |
| Fumed silica Aerosil 350 | 0.23 | 39.2 | 29.6 | 12.4 | 0.3 | 2.1 | 3.4 | 1.4 | 2.3 | 42.5 | 1.3 | 4.5 | 11.6 | 0.02 |
| SBA-15 | 0.23 | 97.8 | 46.6 | 29.4 | 2.3 | 10.5 | 7.0 | 0.1 | 0.5 | 1.8 | 0.4 | 1.6 | 45.6 | 0.06 |
| SBA-16 | 0.23 | 99.0 | 70.5 | 5.8 | 2.8 | 11.2 | 2.6 | 0.3 | 0.9 | 1.5 | 0.7 | 3.7 | 69.8 | 0.09 |

T=325°C, P= 1 atmosphere, 24.3% ethanol in N₂, BD= Butadiene
$^a$DEE= Diethylether
$^b$Others include: acetic acid, butanone, pentanone, C₂-C₅ alkanes, C₆= CO₂, CH₄ and CO
$^c$Productivity= grams of butadiene produced per gram catalyst and per hour

Fig. 4

| SiO₂ support | BET surface (m²/g) | Pore volume (mL/g) | Pore size-adsorption (Angstrom) | Lewis acid sites concentration* (μmoles/g) | Organic impurities level (ppm)** |
|---|---|---|---|---|---|
| Davisil 636 | 442 | 0.84 | 80 | 32.2 | Na:2200 K:270 |
| Large pores Alfa Aesar | 558 | 0.35 | 20 and 100 | 35.0 | Na:2000 K:600 |
| Davisil 646 | 311 | 1.0 | 170 | 22.8 | Na:2400 K:260 |
| Davisil 645 | 299 | 1.1 | 170 | 21.6 | Na:500 K:1850 |
| after K leaching | | | | 27.8 | Na:300 K:100 |
| Davisil 923 | 449 | 0.38 | 40 | 31.0 | Na:2000 K:255 |
| KSKG-GOST 3956-76 | 381 | 0.67 | 75 | 26.1 | Na:5500 K:350 Mg:1100 Ca:3000 Al=3% |
| KSMG-GOST 3956-76 | 475 | 0.26 | 20 and 40 | NA | Na:5500 K:350 Mg:1100 Ca:3000 Al=3% |
| Fumed silica cab-o-sil EL90 | 91 | 1.6 | >200 | NA | Na:2100 K:270 |
| Fumed silica Aerosil 380 | 267 | 1.2 | 300 | 5.0 | Na:2000 K:245 |
| SBA-15 | 728 | 1.1 | 75 | NA | NA |
| SBA-16 | 656 | 1.2 | 50 and 150 | 26.4 | Na:100 K:730 |

*Determined after pyridine adsorption at 50°C and desorption at 150°C
**Determined by ICP

Fig. 5

| Catalyst | Temperature (°C) | WHSV (hr⁻¹) | Conversion (%) | Butadiene selectivity (%) | Butadiene yield (%) | Productivity*** |
|---|---|---|---|---|---|---|
| 1Ag/4ZrO$_2$/SiO$_2$ SBA-16* | 325 | 0.23 | 99.0 | 70.5 | 69.8 | 0.09 |
| 4Ag/4ZrO$_2$/Silica gel 646** | 325 | 0.47 | 89.2 | 73.6 | 61.5 | 0.17 |
| 2Ag/4ZrO$_2$/SiO$_2$** | 320 | 0.3 | 55.2 | 71.3 | 39.4 | 0.07 |
| 2%Zn-8%Y/beta | 330 | 0.3 | 90 | 81.0 | 72.9 | 0.11 |
|  | 350 |  | 100 | 75.0 | 75.0 | 0.12 |
| Cu$_{1.0}$Hf$_{3.0}$Zn$_{0.5}$ | 360 | 0.21 | 99 | 72.0 | 71.6 | 0.09 |

*T = 325°C, P= 1 atmosphere, 24.3% ethanol/N$_2$
**T = 325°C, P= 1 atmosphere, 50%Ethanol/N$_2$
***Productivity= grams of butadiene per gram of catalyst and per hour

Fig. 6

| Catalyst | Conversion (%) | Selectivities (%) | | | | | | | | | | | | |
|---|---|---|---|---|---|---|---|---|---|---|---|---|---|---|
| | | BD | $C_2^=$ | $C_3^=$ | $C_4^=$ | DEE | Ethyl Acetate | Butanol | HAC | Crotonaldehyde | $CH_4$ | CO | $CO_2$ | Others^ |
| 1Ag/4ZrO$_2$/SiO$_2$ | 47.9 | 57.7 | 13.9 | 1.1 | 5.9 | 5.0 | 0.6 | 1.5 | 10.0 | 0.2 | 0 | 0 | 0.4 | 3.7 |
| 1Ir/4ZrO$_2$/SiO$_2$ | 85.4 | 62.8 | 2.0 | 1.8 | 9.9 | 0.6 | 1.7 | 2.0 | 8.9 | 2.2 | 1.3 | 2.2 | 0.3 | 4.2 |
| 1Pt/4ZrO$_2$/SiO$_2$ | 100 | 4.0 | 0.0 | 0.0 | 0.4 | 0.8 | 0.4 | 0.0 | 0.0 | 0.0 | 31.2 | 22.9 | 14.4 | 25.9 |
| T=325°C, P= 1 atmosphere, WHSV = 0.34 hr$^{-1}$, 24.3% ethanol/N$_2$ | | | | | | | | | | | | | | |
| 1Ag/4ZrO$_2$/SiO$_2$ | 76.1 | 75.3 | 3.3 | 1.4 | 4.9 | 1.6 | 2.1 | 1.9 | 5.9 | 0.3 | 0 | 0 | 0.4 | 2.9 |
| 1Ir/4ZrO$_2$/SiO$_2$ | 85.4 | 62.8 | 2.0 | 1.8 | 9.9 | 0.6 | 1.7 | 2.0 | 8.9 | 2.2 | 1.3 | 2.2 | 0.3 | 4.2 |
| 1Pt/4ZrO$_2$/SiO$_2$ | 86.4 | 0.0 | 2.1 | 5.2 | 0.6 | 0.1 | 3.1 | 0.3 | 23.6 | 0.2 | 24.4 | 32.5 | 0.2 | 7.7 |
| T=325°C, P= 1 atmosphere, WHSV varied between 0.23-18.1 hr$^{-1}$, 24.3% ethanol/N$_2$ | | | | | | | | | | | | | | |

^Others include $C_2$-$C_5$ alkanes, $C_5$ olefins, butanone, pentanone, acetic acid. SiO$_2$= Davisil 646
BD= Butadiene, DEE= Diethylether, HAC= acetaldehyde

Fig. 7

| Ag loading (wt %) | WHSV (hr$^{-1}$) | Conversion (%) | Selectivities (%) | | | | | | | | | |
|---|---|---|---|---|---|---|---|---|---|---|---|---|
| | | | Butadiene | $C_2^=$ | $C_3^=$ | $C_4^=$ | DEE* | Ethyl Acetate | Butanol | Acetaldehyde | Crotonaldehyde | Others** |
| 1 | 0.18 | 89.1 | 66.3 | 14.1 | 1.9 | 6.2 | 5.4 | 0.7 | 0.7 | 3.0 | 0.2 | 1.5 |
| 1 | 0.45 | 71.0 | 71.3 | 8.4 | 1.5 | 4.9 | 2.8 | 1.2 | 1.4 | 5.7 | 0.2 | 2.6 |
| 4 | 0.45 | 90.5 | 67.2 | 10.5 | 1.5 | 5.6 | 3.5 | 1.3 | 0.9 | 6.6 | 0.5 | 2.4 |
| 8 | 0.45 | 92.4 | 66.3 | 9.5 | 1.5 | 6.6 | 2.2 | 1.1 | 1.0 | 7.7 | 0.8 | 3.3 |

T= 325°C, P= 1 atmosphere, 24.3% ethanol in $N_2$, $SiO_2$ =Davisil 636
*DEE=Diethylether
**Others= $C_5$ olefins, $C_2$-$C_5$ alkanes, acetic acid, acetone, butanone, pentanone, $CO_2$

Fig. 8

| ZrO₂ loading (wt%) | Lewis acid sites concentration (μmoles/g) | Conversion (%) | Selectivities (%) | | | | | | | | | |
|---|---|---|---|---|---|---|---|---|---|---|---|---|
| | | | BD | C₂= | C₃= | C₄= | DEE | Ethyl Acetate | Butanol | Acetaldehyde | Crotonaldehyde | Others* |
| 1 | 17.3 | 78.6 | 71.2 | 4.1 | 1.0 | 2.4 | 1.3 | 1.4 | 0.8 | 14.2 | 1.1 | 2.5 |
| 2 | 19.2 | 80.6 | 69.8 | 5.1 | 1.0 | 4.1 | 2.1 | 2.1 | 1.4 | 10.7 | 0.9 | 2.8 |
| 4 | 26.0 | 85.9 | 69.1 | 3.7 | 1.2 | 5.5 | 1.6 | 2.9 | 1.8 | 9.2 | 0.7 | 4.3 |
| 10 | 28.4 | 82.3 | 62.4 | 8.4 | 1.3 | 5.7 | 2.5 | 3.1 | 1.7 | 9.3 | 0.8 | 4.8 |

T= 325°C, WHSV = 0.45 hr⁻¹, P= 1 atmosphere, 24.3% ethanol in N₂, SiO₂= Davisil 646
*Others= C₅ olefins, C₂-C₅ alkanes, acetic acid, acetone, butanone, pentanone, CO₂. Acid sites determined after pyridine desorption at 150°C.
BD= Butadiene, DEE= Diethylether

Fig. 9

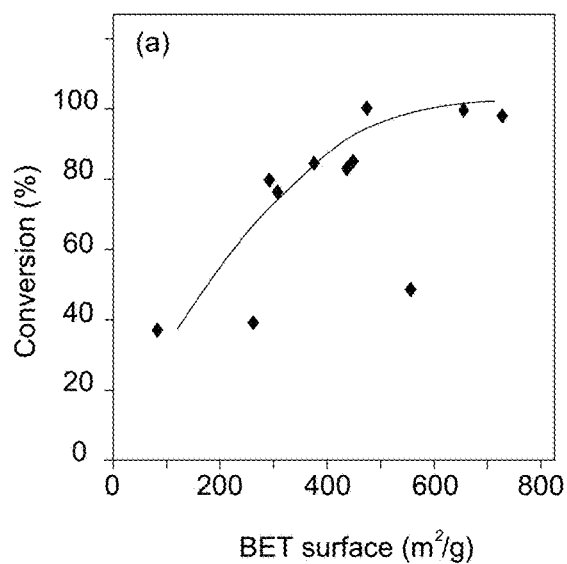
10(a)
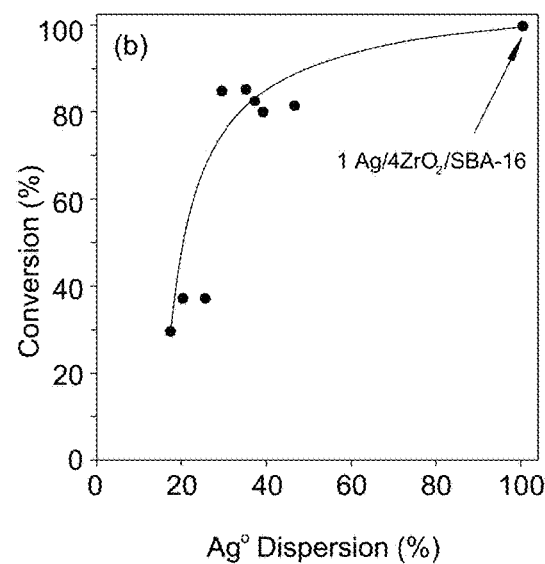
10(b)
Fig. 10

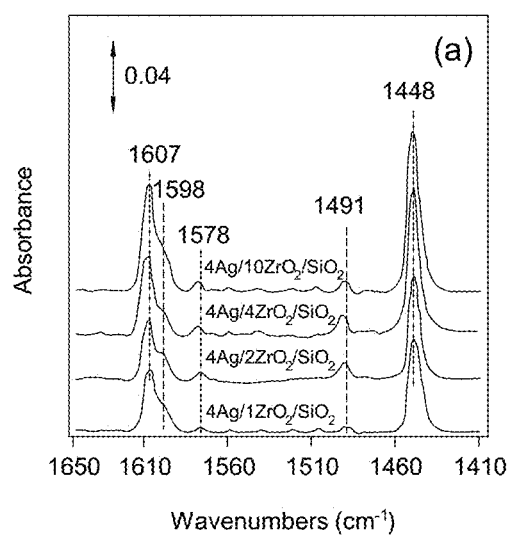 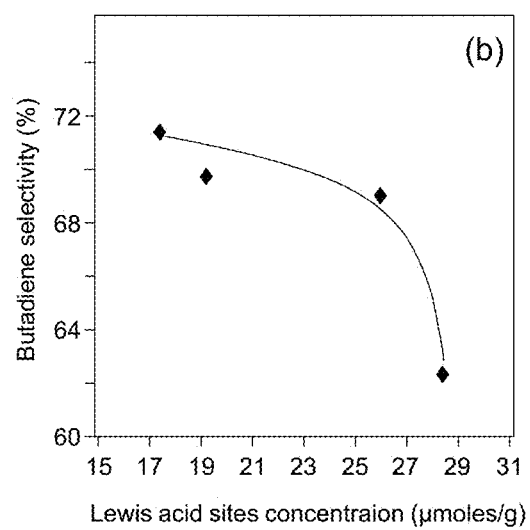
12(a) 12(b)
Fig. 12

| ZrO₂ loading (wt%) | Conversion (%) | Selectivities (%) | | | | | | | | | |
|---|---|---|---|---|---|---|---|---|---|---|---|
| | | BD | C₂= | C₃= | C₄= | DEE | Ethyl Acetate | Butanol | Acetaldehyde | Crotonaldehyde | Others* |
| 1 | 78.6 | 71.2 | 4.1 | 1.0 | 2.4 | 1.3 | 1.4 | 0.8 | 14.2 | 1.1 | 2.5 |
| 2 | 80.6 | 69.8 | 5.1 | 1.0 | 4.1 | 2.1 | 2.1 | 1.4 | 10.7 | 0.9 | 2.8 |
| 4 | 85.9 | 69.1 | 3.7 | 1.2 | 5.5 | 1.6 | 2.9 | 1.8 | 9.2 | 0.7 | 4.3 |
| 10 | 82.3 | 62.4 | 8.4 | 1.3 | 5.7 | 2.5 | 3.1 | 1.7 | 9.3 | 0.8 | 4.8 |

T= 325°C, WHSV ethanol = 0.45 hr⁻¹, P = 1 atmosphere, 24.3% ethanol in N₂
*Others= C₆ olefins, C₂-C₅ alkanes, acetic acid, acetone, MEK, CO₂, heavy compounds.
BD= Butadiene, DEE=Diethylether 14(a)

| ZrO₂ loading (wt%) | Lewis Acid sites (μmoles/g) | | |
|---|---|---|---|
| | 150°C | 250°C | 350°C |
| 1 | 17.3 | 6.7 | 4.2 |
| 2 | 19.2 | 4.3 | 2.8 |
| 4 | 26.0 | 8.3 | 6.2 |
| 10 | 28.4 | 8.1 | 5.8 |

Acid sites determined after adsorption- desorption of pyridine followed by IR spectroscopy 14(b)

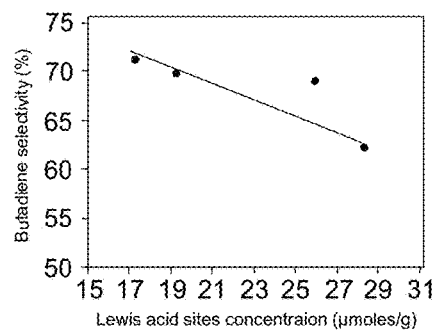

| Treatment of the support | K loading ppm | Conversion (%) | Selectivity (%) | | | | | | | | | |
|---|---|---|---|---|---|---|---|---|---|---|---|---|
| | | | BD | $C_2=$ | $C_3=$ | $C_4=$ | DEE | EA | BuOH | HAC | Crotonaldehyde | Others* |
| Technical grade. No treatment | 2000 | 29.5 | 41.6 | 15.9 | 1.2 | 3.7 | 4.7 | 0.6 | 3.8 | 12.4 | 0.5 | 15.6 |
| After ion-exchange with 100mL of $NH_4OH$ solution | <100ppm | 79.6 | 73.4 | 5.3 | 1.7 | 5.1 | 1.8 | 1.8 | 1.4 | 5.0 | 0.7 | 4.0 |
| After ion-exchange with 50mL of $NH_4OH$ solution | <100ppm | 88.9 | 75.0 | 4.7 | 1.7 | 5.8 | 1.6 | 1.7 | 1.7 | 4.1 | 0.5 | 3.2 |
| After ion-exchange with 25mL of $NH_4OH$ solution | <100ppm | 89.0 | 75.2 | 5.5 | 0 | 6.1 | 1.9 | 1.5 | 1.5 | 4.5 | 0.6 | 3.2 |
| After ion-exchange with 10mL of $NH_4OH$ solution | <100ppm | 85.6 | 74.2 | 6.4 | 1.8 | 4.8 | 2.3 | 1.3 | 1.3 | 4.2 | 0.7 | 3.0 |
| After ion-exchange with 1mL of $NH_4OH$ solution | <100ppm | 82.4 | 74.0 | 8.1 | 1.9 | 4.7 | 3.0 | 0 | 1.7 | 4.2 | 0.7 | 1.7 |
| Washed with 100mL $NH_4OH$ and added K by impregnation | 300ppm | 86.7 | 74.2 | 3.2 | 1.9 | 5.9 | 1.1 | 2.0 | 1.6 | 4.5 | 0.9 | 4.5 |

T= 325°C, P= 1 atmosphere, 24.3% ethanol in $N_2$, WHSV ethanol = 0.23 $hr^{-1}$,
*Others= $C_5$ olefins, $C_2$-$C_5$ alkanes, MEK, $CO_2$, acetone, acetic acid, heavy compounds.
BD= Butadiene, DEE= Diethylether, EA= Ethyl acetate, BuOH= butanol, HAC= Acetaldehyde

Fig. 15

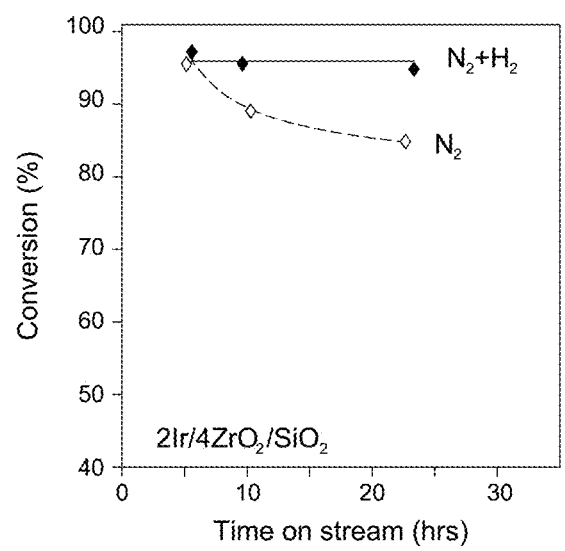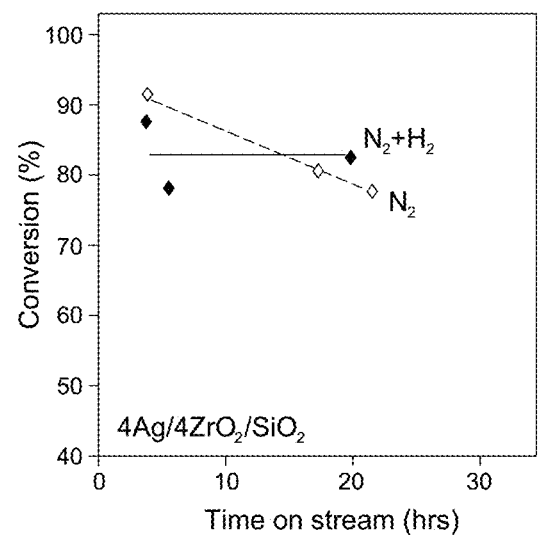
Fig. 16

| WHSV hr-1 | Conversion % | BD | $CO_2$ | $C_2=$ | $C_3=$ | $C_4=$ | DEE | EA | BuOH | HAC | Crotonaldehyde | Acetone | AA | Others* |
|---|---|---|---|---|---|---|---|---|---|---|---|---|---|---|
| 0.13 | 98.9 | 54.0 | 1.7 | 14.4 | 5.0 | 7.3 | 0.3 | 1.4 | 0.5 | 9.6 | 0.7 | 1.2 | 2.6 | 1.3 |
| 0.37 | 96.8 | 51.2 | 1.8 | 7.7 | 3.8 | 4.1 | 0.2 | 0.2 | 0.6 | 17.9 | 1.3 | 1.6 | 4.2 | 5.4 |
| 0.74 | 89.0 | 47.5 | 1.0 | 6.5 | 2.8 | 3.0 | 0.2 | 0.7 | 1.0 | 24.9 | 1.8 | 0.9 | 4.3 | 5.4 |

*Others = C2-C5 alkanes, butyraldehyde, methyl acetate, Ethyl acetate, methanol, propanol, butanone, pentanone.
BD= Butadiene, $C_2=$ ethylene, $C_3=$ propylene, $C_4=$ butenes, DEE= Diethyl ether, EA= Ethyl acetate, BuOH= butanol, HAC= acetaldehyde, AA= acetic acid

Fig. 17

| Feed | Conversion % | Selectivities (%) | | | | | | | | | | | | |
|---|---|---|---|---|---|---|---|---|---|---|---|---|---|---|
| | | BD | $CO_2$ | $C_2=$ | $C_3=$ | $C_4=$ | DEE | EA | BuOH | HAC | Crotonaldehyde | Acetone | AA | Others* |
| 100% EtOH | 95.1 | 56.4 | 0.6 | 25.4 | 3.4 | 8.8 | 0.4 | 0.4 | 0.3 | 0.4 | 0.0 | 0.2 | 1.2 | 2.5 |
| 95% EtOH 5% $H_2O$ | 94.4 | 49.0 | 0.3 | 33.6 | 2.9 | 7.3 | 3.1 | 0.3 | 0.0 | 0.9 | 0.0 | 0.0 | 1.1 | 1.5 |
| 35% EtOH 65% $H_2O$ | 96.8 | 51.3 | 1.8 | 7.7 | 3.9 | 4.1 | 0.2 | 0.2 | 0.6 | 17.9 | 1.3 | 1.6 | 4.2 | 5.2 |

*Others = C2-C5 alkanes, butyraldehyde, methyl acetate, methanol, propanol, butanone, pentanone.
BD= Butadiene, $C_2$= ethylene, $C_3$= propylene, $C_4$= butenes, DEE= Diethyl ether, EA= Ethyl acetate, BuOH= butanol, HAC= acetaldehyde, AA= acetic acid

Fig. 18

| Feed | Conversion % | Selectivities (%) | | | | | | | | | | | | |
|---|---|---|---|---|---|---|---|---|---|---|---|---|---|---|
| | | BD | $CO_2$ | $C_2=$ | $C_3=$ | $C_4=$ | DEE | EA | BuOH | HAC | Crotonaldehyde | Acetone | AA | Others* |
| 100% EtOH | 82.8 | 67.5 | 0.4 | 9.0 | 1.5 | 5.7 | 3.1 | 3.2 | 0.4 | 4.2 | 0.0 | 0.0 | 3.2 | 1.8 |
| 95% EtOH 5% $H_2O$ | 76.4 | 67.8 | 0.2 | 11.0 | 1.6 | 4.9 | 4.0 | 3.6 | 0.2 | 3.0 | 0.1 | 0.0 | 1.2 | 2.4 |
| 35% EtOH 65% $H_2O$ | 51.9 | 49.0 | 0.5 | 3.2 | 1.4 | 1.8 | 0.7 | 2.5 | 1.7 | 32.5 | 2.3 | 0.4 | 2.2 | 1.8 |

*Others = C2-C5 alkanes, butyraldehyde, methyl acetate, methanol, propanol
BD= Butadiene, $C_2$= ethylene, $C_3$= propylene, $C_4$= butenes, DEE= Diethyl ether, EA= Ethyl acetate, BuOH= butanol, HAC= acetaldehyde, AA= acetic acid

Fig. 19

| Ethanol % in $N_2$ | Conversion % | Productivity* | BD | $C_2=$ | $C_3=$ | $C_4=$ | DEE | EA | BuOH | HAC | Crotonaldehyde | Others** |
|---|---|---|---|---|---|---|---|---|---|---|---|---|
| 24.3 | 85.9 | 0.16 | 69.1 | 3.7 | 1.2 | 5.5 | 1.6 | 2.9 | 1.8 | 9.2 | 0.7 | 4.3 |
| 50.6 | 81.6 | 0.32 | 69.9 | 3.1 | 1.0 | 5.6 | 1.7 | 1.5 | 1.4 | 10.3 | 0.9 | 4.6 |
| 77.0 | 76.9 | 0.45 | 69.4 | 2.9 | 0.9 | 4.8 | 1.3 | 0.7 | 1.4 | 11.4 | 1.3 | 5.9 |

*Productivity= grams of butadiene per gram of catalyst and per hour
**Others = acetic acid, C2-C5 alkanes, butyraldehyde, methyl acetate, methanol, propanol, butanone, pentanone.
BD= Butadiene, $C_2=$ ethylene, $C_3=$ propylene, $C_4=$ butenes, DEE= Diethyl ether, EA= Ethyl acetate, BuOH= butanol, HAC=acetaldehyde

Fig. 20

SINGLE STEP CONVERSION OF ETHANOL TO BUTADIENE

CLAIM TO PRIORITY

This application claims priority from provisional patent No. 62/455,768 filed by the same applicant and inventors on Feb. 7, 2017. The contents of which are incorporated by reference in their entirety.

STATEMENT AS TO RIGHTS TO INVENTIONS MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

BACKGROUND OF THE INVENTION 1,3-Butadiene (BD) is an important building block used in the polymer chemistry. It is used among other things in the production of styrene-butadiene rubbers that are primarily used in the fabrication of materials such as synthetic rubber or elastosmers which make up products such as production of polymers such as synthetic rubbers or elastomers including styrene-butadiene rubber (SBR), polybutadiene rubber (PBR), nitrile rubber (NR) and polychloropropene (Neoprene).

Currently, BD is typically primarily obtained as a by-product of the naphtha steam cracking process that serves to make ethylene. The production of ethylene from steam cracking is in decline due to the recent and drastic increase of shale gas production in the USA which offers another pathway for obtaining ethylene from ethane but does not result in the BD creation. In addition to the shift in lighter feedstocks, crude oil price swings have historically led to corresponding price fluctuations in the cost of butadiene, and this is not sustainable for the end users of this important building block. Thus, alternative technologies for producing butadiene are highly desired.

Ethanol conversion to butadiene (ETB) represents an attractive alternative technology. Ethanol can be sourced from a variety of locations including commercial production from renewable biomass or waste sources. In addition, the ethanol "blend wall" coupled with advancements in production efficiency and feedstock diversification will potentially lead to excess ethanol at competitive prices available for the production of a wide range of fuels and commodity chemicals. Furthermore a recent early-stage assessment method comparing the bioethanol-based pathway for butadiene production with the naphtha-based route suggests that the bioethanol pathway could be a promising alternative to the naphtha-based process.

Research on butadiene production from ethanol has existed for years however, achieving high yield to butadiene at industrially relevant process conditions has been challenging. There are a large number of catalyst systems capable of converting ethanol to butadiene in one step that have been reported however, in many of these instances low single pass conversion (<45%) resulted. For the single-step process to be successful and viable higher per pass conversion and high selectivity (≥70%) are desirable. What is needed is a system for producing BD from ethanol that can achieve this higher selectivity in a single pass. The present disclosure provides examples of advances toward meeting this need.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY

The present disclosure provides examples of a process for producing 1,3-butadiene (BD) from ethanol in a single step by passing a mixture containing ethanol in a gas phase over a multifunctional catalyst having a transition metal dispersion of at least 30% on a metal oxide support. In some examples the multifunctional catalyst is a ternary catalyst comprising a silica metal oxide having a surface area of at least 200 m^2/g. The multifunctional catalyst could also be a transition metal oxide including for example; a silver (Ag) metal oxide, a silica metal oxide made from a high purity silica gel, mesoporous silica and fumed silica, such as high purity SBA16, SBA15, or Davisil grade 646.

In some examples, hydrogen can be added to the mixture. The mixture may also include water in addition to ethanol in a percentage ranging between 10 and 100 percent. In one particular example the mixture is 35% ethanol and includes water. The processing conditions in which the temperature ranges between 200° C. and 500° C., the pressure between 1 atm and 20 atm and a weight-hour space velocity between 0.05 and 20 hr$^{-1}$.

In one particular example a process for producing 1,3-butadiene (BD) from ethanol in a single step is described wherein a mixture containing ethanol in a gas phase is passed over a ternary Ag/ZrO2/SiO2 catalyst having a transition metal dispersion of at least 30% on a silica metal oxide support. In one example the ternary catalyst is 1% Ag/4% ZrO2/SiO2-SBA-16. In other examples the operating conditions include a temperature of 325° C., pressure of 1 atm, and a flow rate of 0.23 hr-1. In some other examples the mixture contains water and less than 50% ethanol.

Various additional advantages and novel features of the present invention are described herein and will become further readily apparent to those skilled in this art from the following detailed description and attached presentations. In the preceding and following descriptions only a sampling of the embodiments of the invention are shown by way of illustration. Accordingly, the descriptions and presentations of the preferred embodiment are to be regarded as illustrative in nature, and not as restrictive.

BRIEF DESCRIPTION OF THE DRAWINGS

FIG. 3 shows reactivity performance for various catalytic embodiments.

FIG. 4 shows effect of the SiO2 support on the catalytic performance of 1Ag/4ZrO2/SiO2 catalysts.

FIG. 5 shows BET Surface, pore volume, pores size, Lewis acid sites concentration, organic impurities contents for 1Ag/4ZrO2/SiO2 catalysts synthesized from different SiO2 supports.

FIG. 6 shows catalytic performance comparison between catalysts under similar reaction conditions (T=320-350° C., WHSV=0.2-0.5 hr$^{-1}$, P=1 atmosphere).

FIG. 7 shows effect of the nature of the metal Ag, Pt or Ir on the catalytic performance FIG. 8 shows effect of the Ag loading on the catalytic performance of Ag/4ZrO2/SiO2 catalysts.

FIG. 9 shows effect of the ZrO2 loading on the catalytic performance for 4Ag/yZrO2/SiO2 catalysts and Lewis acid sites concentration FIG. 10 shows evolution of the conversion with (a) the BET surface and (b) the Ag dispersion for 1Ag/4ZrO2/SiO2 catalysts prepared from different silicas. The dispersion was measured via TEM after reduction. T=325° C., WHSV=0.23 hr$^{-1}$, P=1 atmosphere, 24.3% ethanol in N2.

FIG. 12 shows infrared spectra recorded after pyridine adsorption at 50° C. followed by desorption at 150° C. for 4Ag/yZrO2/SiO2 (Davisil 646) catalysts; varying the ZrO$_2$ loading (y=1-10 wt. %). Spectra were normalized to a pellet of 20 mg and 2 cm2. (b) Evolution of the butadiene selectivity with the concentration of Lewis acid sites determined after pyridine desorption at 150° C.

FIG. 14 presents the results of ZrO$_2$ on stability of the catalyst compositions FIG. 15 shows the results of washing to remove K on various example catalysts.

FIG. 16 shows the results of hydrogen to the processing conditions. T=325° C., WHSV=0.23 hr$^{-1}$, P=1 atmosphere, 24.3% ethanol in N$_2$ or N$_2$/H$_2$ mixture. SiO$_2$ support: Davisil 646.

FIG. 17 shows a set of data related to the addition of water to the process mixture feed and the effect of weight-hour space velocity. T=400° C., P=1 atmosphere, 35% ethanol in H$_2$O feed mixture. 4% Ag/4% ZrO$_2$/SiO$_2$ (Davisil 646).

FIG. 18 shows another data set related to the addition of water to a process mixture feed. T=400° C., WHSV=0.30-0.35 hr–1, P=1 atmosphere. 4% Ag/4% ZrO$_2$/SiO$_2$ (Davisil 646).

FIG. 19 shows the shows another data set related to the addition of water a process mixture feed. T=325° C., WHSV=0.30-0.35 hr–1, P=1 atmosphere. 4% Ag/4% ZrO$_2$/SiO$_2$ (Davisil 646).

FIG. 20 shows a data set related to the dilution of carrier gas nitrogen on conversion. T=325° C., GHSV=911 hr$^{-1}$, WHSV$_{ethanol}$=0.45-1.44 hr$^{-1}$, P=1 atmosphere. 4% Ag/4% ZrO$_2$/SiO$_2$ (Davisil 646).

DETAILED DESCRIPTION OF THE INVENTION

The following description includes examples of various modes of the present disclosure. It will be clear from this description of the disclosure that the disclosure is not limited to these illustrated embodiments but that the disclosure also includes a variety of modifications and embodiments thereto. Therefore the present description should be seen as illustrative and not limiting. While the disclosure is susceptible of various modifications and alternative constructions, It should be understood, that there is no intention to limit the disclosure to the specific form disclosed, but, on the contrary, the disclosure is to cover all modifications, alternative constructions, and equivalents falling within the spirit and scope of the disclosure as defined in the claims.

Figure 1:
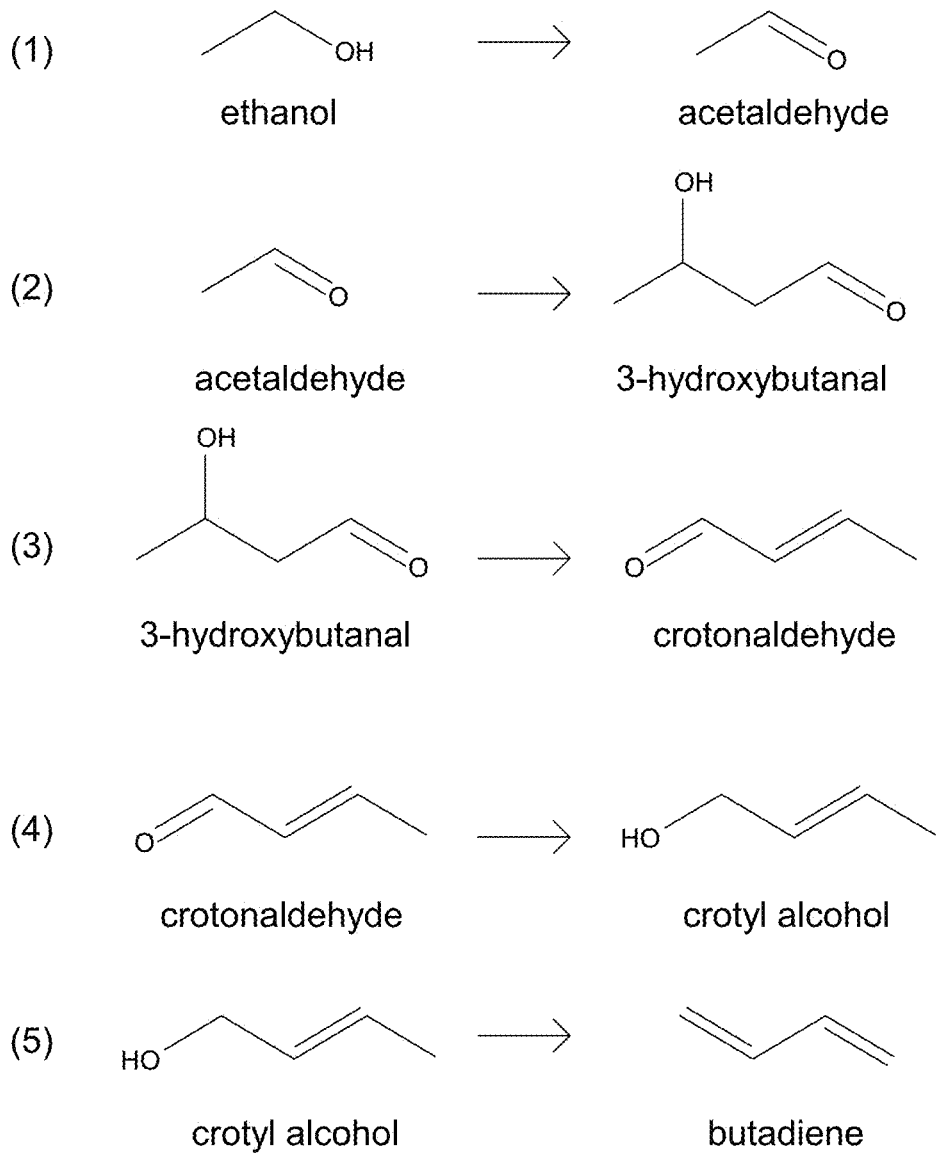
FIG. 1 shows the generally accepted reaction pathway for the formation of butadiene from ethanol. By-products are not included.
Figure 2:
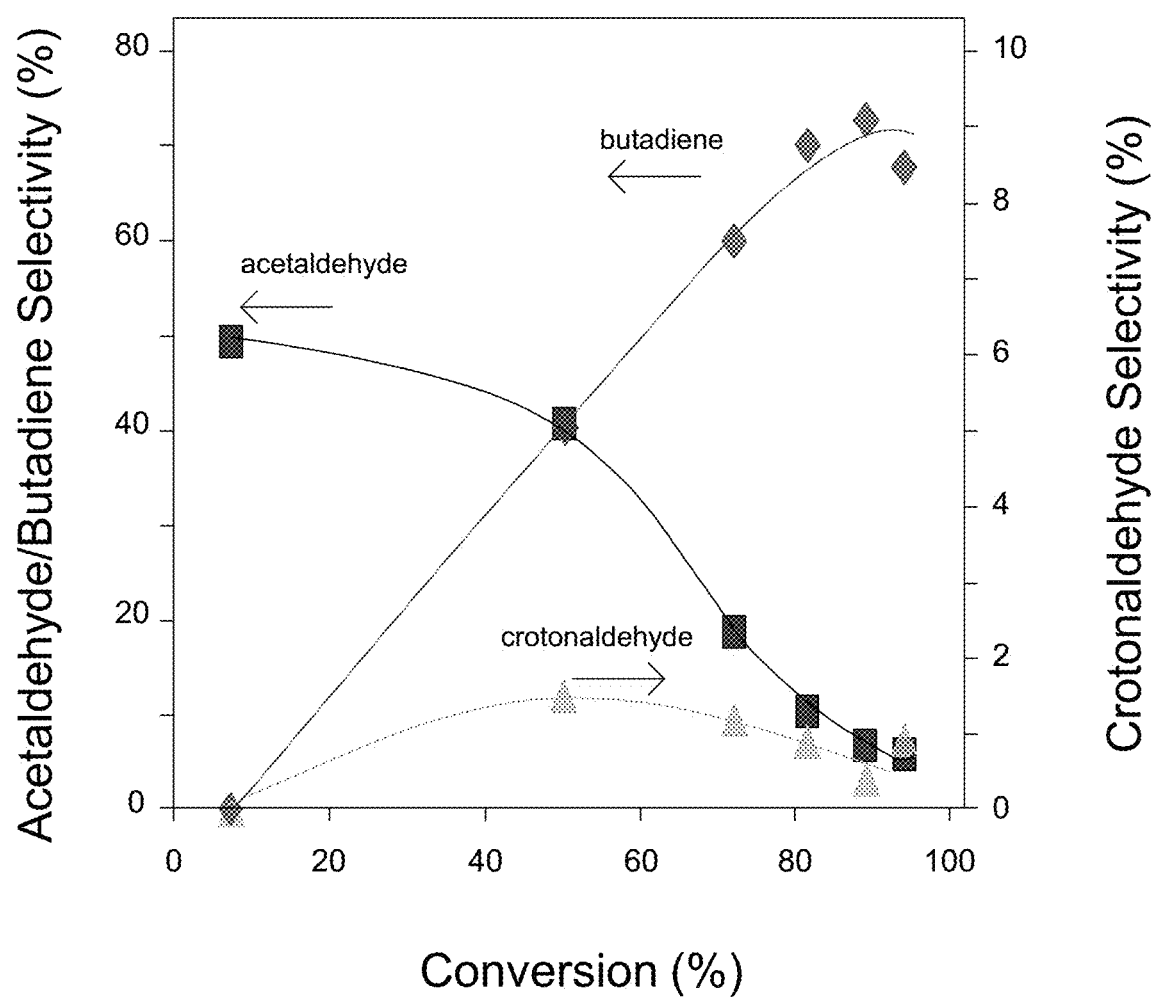
FIG. 2 shows the selectivities to butadiene, acetaldehyde and crotonaldehyde as a function of the conversion over 4Ag/4ZrO2/SiO2 (Davisil 646) catalyst. T=325° C., P=1 atmosphere, WHSV=0.37-38.0 hr$^{-1}$, 50% ethanol/N2.
Figure 11:
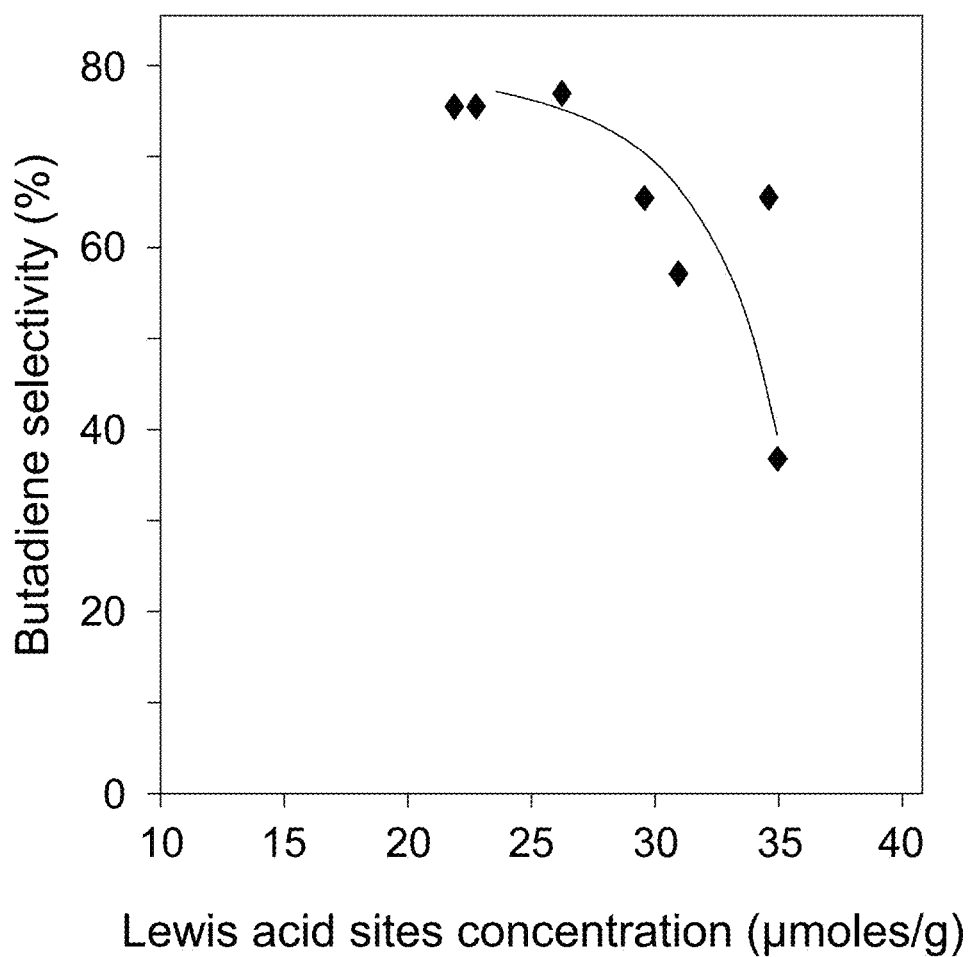
FIG. 11 shows evolution of the butadiene selectivity with the Lewis acid sites concentration for 1Ag/4ZrO2/SiO2 catalysts. Lewis acid sites concentration determined after pyridine desorption at 150° C. Butadiene selectivity at 75-85% conversion.

The reaction mechanism for the conversion of ethanol to butadiene has generally been accepted as the reaction pathway presented in FIG. 1 and involves ethanol dehydrogenation to acetaldehyde, followed by acetaldehyde condensation to 3-hydroxybutanal and its subsequent dehydration to crotonaldehyde, reduction of crotonaldehyde to crotyl alcohol, and finally its dehydration to butadiene. FIG. 2 shows the evolution of selectivity curves for these various compounds in one particular example.

The table in FIG. 3 shows a series of ternary Ag/ZrO2/SiO2 catalysts were studied for the single-step conversion of ethanol to butadiene (ETB). While Ag plays a major role in the ethanol conversion to acetaldehyde, the Lewis acid sites appeared to be responsible for the conversion of acetaldehyde to butadiene. Adding H$_2$ to the feed gas does not affect the initial conversion, however, the selectivities to butadiene and butenes (i.e., 2-butene and 1-butene) are impacted. While SBA-15 and SBA-16 demonstrated increased activity in achieving almost full conversion large differences in selectivities to the main products are observed between the two catalysts. The butadiene selectivity is equal to 46.6% and 70.5% for 1Ag/4ZrO$_2$/SiO$_2$ SBA-15 and 1Ag/4ZrO$_2$/SiO$_2$ SBA-16, respectively. The ethylene selectivity is quite high for the 1Ag/4ZrO$_2$/SiO$_2$ SBA-15 catalyst and equal to 29.4% whereas it is equal to 5.8% for 1Ag/4ZrO$_2$/SiO$_2$ SBA-16. Among all the catalysts tested, the 1Ag/4ZrO$_2$/SiO$_2$ SBA-16 is the most active toward butadiene formation and a butadiene yield equal to 70% was obtained. These experiments show the strong influence of the nature of the SiO$_2$ support has on the catalytic performance of Ag/ZrO$_2$/SiO$_2$ catalysts for butadiene production from ethanol. Indeed, conversion between ~30 and 100% and butadiene yield between 0 and 70% can be obtained depending of the nature of the SiO$_2$ support.

The table in FIG. 4 shows the effect of SO$_2$ support in the catalytic performance of 1Ag/4ZrO$_2$/SiO$_2$ catalysts. A total of 11 1Ag/4ZrO$_2$/SiO$_2$ catalysts supported on different SiO$_2$ were tested under similar reaction conditions. (T=325 degrees C., WHSV 0.23/hr, P=1 atm, 24.3% ethanol feed in N2). Differences in conversion and selectivities were observed depending on the choice of SiO$_2$ support, and the surface area of the SiO$_2$ appears to have a direct impact on the conversion which increases with the SiO$_2$/catalyst surface area due to increased Ag dispersion. The butadiene selectivity varies also greatly depending on the SiO$_2$ support. The tables in FIGS. 5-9 as well as the graphs shown in FIGS. 10-21 provide additional performance data regarding these catalysts.

The interaction between SiO$_2$ and ZrO$_2$ differs depending on the SiO$_2$ support which affects the catalyst acidity and consequently the butadiene selectivity. The catalysts were characterized by means of N$_2$ adsorption, Pyridine adsorption/desorption followed by FTIR spectroscopy and induced coupled plasma. These silica gels present different BET surface between 299 m$^2$/g and 558 m$^2$/g with a pore size decreasing from 120-170 Angstrom for the catalyst with the lowest BET surface to about 20-40 Angstrom for the catalysts with the highest BET surfaces. In comparison, the two fumed silicas present a lower surface area (i.e. <270 m$^2$/g)

with large pores (i.e. >200 angstrom). Both mesoporous $SiO_2$ have large BET surface (i.e., 656-728 m2/g) but different pore sizes (70 Angstrom for SBA-15 and 20 and 150 Angstrom for SBA-16). The acidity measurements indicate large differences between the catalysts as the one synthesized from the fumed silica Aerosil 390 has a concentration of Lewis acid sites equal to only 5 µmoles/g whereas the one supported on the Alfa Aeser silica gel presents a Lewis acid sites concentration of 35 µmoles/g.

Large differences in conversion percentages were reported among the various materials. The conversion varied from 29.5% for the $1Ag/4ZrO_2$ catalyst supported on Davisil 645 (before ion-exchange) to 100% conversion for the one supported on KSMG-GOST 3956-76. The products selectivities vary also greatly depending of the silica gel support. For instance, a butadiene selectivity as low as 29.3% was measured for the catalyst supported on the Alfa Aeser silica gel as opposed to 78.3% butadiene selectivity for the one supported on KSKG-GOST 3956-76. The catalysts prepared from the silica gel 645 and 646 present similar BET surface, pore volume, pore size and acid sites concentration. However, when tested under the same reaction conditions, the conversion and butadiene selectivities are significantly higher for the $1Ag/4ZrO_2/SiO_2$ Davisil 646.

The Davisil 645 silica gel presents a higher content of K (i.e. 1850 ppm) as compared to the Davisil 646 (i.e. 260 ppm). To test the hypothesis that that the K impurity impedes the ethanol conversion an ion-exchange was done for the Davisil 645. The K level was decreased to ~100 ppm after ion-exchange. The $1Ag/4ZrO_2$ catalysts supported on the ion-exchanged Davisil 645 presents a conversion of 79.6% and a selectivity to butadiene equal to 73.4% which is similar to the results obtained for the $1Ag/4ZrO_2/SiO_2$ Davisil 646 catalysts. Hence, these results suggest that K impurity inhibits the ethanol conversion, by altering occupying locations that would otherwise form acid sites on the support.

As discussed above, acid sites are responsible for the acetaldehyde conversion to butadiene and intermediates. The Lewis acid sites concentration of the $1Ag/4ZrO_2/SiO_2$ fumed silica Aerosil 380 is low and equal to 5 µmoles/g which can explain the high selectivity toward acetaldehyde.

The evidence in these tables reflects the fact that SBA-16 surpasses other $SiO_2$ support as evidenced by excellent catalytic performance attained over a $1Ag/4ZrO_2/SiO_2$-SBA-16 catalyst thus resulting in a ~70% butadiene yield and ~90% yield of total olefins at 99% ethanol conversion while operating under mild conditions (325° C., 1 atm, 0.23 $hr^{-1}$). By varying independently the Ag loading and the $ZrO_2$ loading, it was found that the optimal composition for a silica gel supported catalyst is 4 wt % Ag and 4 wt % $ZrO_2$. In these experiments a direct relationship between butadiene selectivity and concentration of Lewis acid sites was also demonstrated. Butadiene selectivity appears to decrease with increasing Lewis acid sites concentration. Catalyst stability study shows a decrease of conversion over time due to coking. Efficient catalyst regenerability was successfully demonstrated for multiple cycles.

FIGS. 10(a) and 9(b) chart the effects of BET surface on ethanol to butane conversion over the $Ag/4ZrO_2/SiO_2$ catalysts prepared from different silicas. Addition of $H_2$ to the feed gas favors hydrogenation reactions and can impede oligomerization reactions as well as dehydrogenation reactions leading to the formation of aromatics. Addition of $ZrO_2$ (metal oxide with acid sites) to $Ag/SiO_2$ did not appear to have a significant impact on the ETB conversion, however ETB conversion generally did tend to increase with the catalyst surface area. It is believed that this increase of the ETB conversion is attributed to a better dispersion of Ag with the increase of the surface area. Thus accounting for the direct relationship between the butadiene selectivity and the concentration of Lewis acid sites.

Depending of the nature of the $SiO_2$ support, the concentration of the acid sites responsible for the conversion of acetaldehyde to butadiene varies greatly for various catalysts including $Ag/ZrO_2/SiO_2$ catalysts. However, $SiO_2$ alone is not responsible for the catalyst acidity. The bare $SiO_2$ produced mainly acetaldehyde from ethanol and $ZrO_2$ is required to produce butadiene. The interaction between $ZrO_2$ and $SiO_2$ varies greatly depending of the nature of the $SiO_2$ support which ultimately affects the catalyst acidity and butadiene selectivity. TEM imaging and XRD analysis demonstrate the presence of Zr widely dispersed over the $SiO_2$ support in the most effective catalysts. These results suggest that Zr is actually present as $ZrO_x$ patches interacting with $SiO_2$ support modifying the catalyst acidity.

The catalysts acidity was investigated by pyridine adsorption/desorption followed by Infrared spectroscopy to determine the nature and the concentration of the acid sites. The results of these studies did tend to show that acid sites play a role in the conversion of acetaldehyde to butadiene. The infrared spectra evidenced the presence of Lewis acid sites but no band characteristic of Brönsted acid sites was detected for any of the $1Ag/4ZrO_2/SiO_2$ catalysts prepared from silica gels, fumed silicas and mesoporous silicas. The relationship between the butadiene selectivity and the Lewis acid sites concentration for the $1Ag/4ZrO_2/SiO_2$ catalysts presents a similar conversion between 75-85%. As shown in the figures, butadiene selectivity decreases from ~75% to ~30% as the Lewis acid sites concentration increases from ~22 umoles/g to ~35 umoles/g. These results suggest a relationship between butadiene selectivity and the amount of Lewis acid sites. In addition, they indicate that lower Lewis acid site concentrations are preferred to obtain higher selectivity to butadiene.

The catalytic performance of the $1Ag/4ZrO_2/SiO_2$ (Davisil 646) catalyst was compared when promoting with either Pt or Ir precious metal, in lieu of Ag. Under the same reaction conditions, the activity is the highest for the supported Pt catalyst since full conversion was achieved. The table in FIG. 7 shows the effect of Ag loading on the catalytic performance of $Ag/4ZrO_2/SiO_2$ catalysts. (The Ag dispersion was calculated from the Ag particle size using the formula D %=100/d where D represents the dispersion and d stands for the Ag particle size. A total number of 100 particles was analyzed to determine the Ag particle size of each catalyst.) The conversion clearly increases from 71% to 90.5% when the Ag loading increases from 1 to 4% but for Ag>4% the conversion increases only slightly to 92.4%. The space velocity was varied for the $1Ag/4ZrO_2/SiO_2$ catalyst to compare the main products selectivity at similar conversion (i.e., ~89-82%). The main reaction products include butadiene, ethylene, DEE, acetaldehyde and butenes (i.e., 1-butene, 2-butene). At similar conversion, the butadiene selectivity is equal to ~66-67% for all three catalysts. Similarly, the butenes selectivity is quite similar for the three catalysts and between ~5.6-6.6%. Both ethylene and DEE selectivities decrease notably with the increase of the Ag loading from 1 to 4%.

Ethylene selectivity decreases from 14.1% for $1Ag/4ZrO_2/SiO_2$ to 10.5% for $4Ag/4ZrO_2/SiO_2$. However, for Ag loading >4% only a slight decrease of ethylene and DEE selectivities is observed. The acetaldehyde selectivity increases from 3% to 7.7% when the Ag loading increases from 1 to 8%. As demonstrated above, Ag is responsible for the dehydrogenation of ethanol to acetaldehyde. The increase of Ag loading leads to an increased amount of active sites for ethanol dehydrogenation. This can explain the increase of the acetaldehyde selectivity. Overall, 4Ag/4ZrO$_2$/SiO$_2$ is more active than 1Ag/4ZrO$_2$/SiO$_2$. The two catalysts with 4 and 8% Ag present similar activity and selectivity. Since lower metal loading reduces the cost of the catalyst we have chosen to investigate the effect of ZrO$_2$ loading for a 4Ag/yZrO$_2$/SiO$_2$ catalyst.

FIG. 12 (a) displays the normalized infrared spectra recorded after pyridine adsorption at 50° C. followed by desorption at 150° C. between 1410-1550 cm−1 for the 4Ag/yZrO2/SiO2 catalysts with ZrO2 loading between 1 and 10 wt. %. Two bands located at 1448 and 1491 cm−1 corresponding to coordinated pyridine and characteristic of Lewis acid sites are detected. The increase of the intensity of these bands with the ZrO2 loading is indicative of an increase of the concentration of the Lewis acid sites. Note that the spectra do not evidence the presence of Brönsted acid sites since no band located at ~1540 cm−1 is detected. However, the presence of a minor amount of Brönsted acid sites cannot be completely ruled out. Indeed, the catalysts may contain a minor amount of Brönsted acid sites that are not sufficiently strong to protonate pyridine.

The concentration of Lewis acid increases from 17.3 μmoles/g for 4Ag/1ZrO$_2$/SiO$_2$ to 28.4 μmoles/g for 4Ag/10ZrO$_2$/SiO$_2$. The results do not clearly evidence a relationship between the concentration of the acid sites and conversion. The conversion increases slightly from ~79 to ~86% when the Lewis acid sites concentration increases from 17.3 to 26 μmoles/g and further increase of the amount of acid sites results in a decrease of the conversion. FIG. 6 (b) presents the evolution of the butadiene selectivity with the Lewis acid sites concentration. One can see that the butadiene selectivity decreases from about 71% to 62% with the increase of the Lewis acid sites concentration. Among all the 4Ag/ZrO$_2$ catalysts supported on SiO$_2$ Davisil 646, 4Ag/4ZrO$_2$/SiO$_2$ (Davisil 646) presents the highest yield toward butadiene (59.4%).

To address potential concerns regarding coking various experiments and tests were performed particularly in regard to the stability and regenerability of 1Ag/4ZrO$_2$/SiO$_2$ (SBA-16). The results are displayed in FIG. 13. As shown in this figure, the conversion decreases from 98% (TOS=5 hours) to 81% after 22 hours on stream. However, the butadiene selectivity remains fairly stable at approximately 70%. The deactivation is likely due to coking from heavy compounds as aromatics liquid product were detected when notable drops of conversion occurred. Two successful regeneration cycles were conducted under flowing 5% O$_2$/He for 4-5 hours at 500° C. followed by a reduction treatment at 325° C. under 10% H$_2$/N$_2$ for 1 hour. Indeed, after the oxidation/reduction treatment the catalyst regains its initial conversion. This highlights the effectiveness of this oxidative treatment for complete regeneration of the Ag/ZrO$_2$/SiO$_2$ system.

Figure 13:
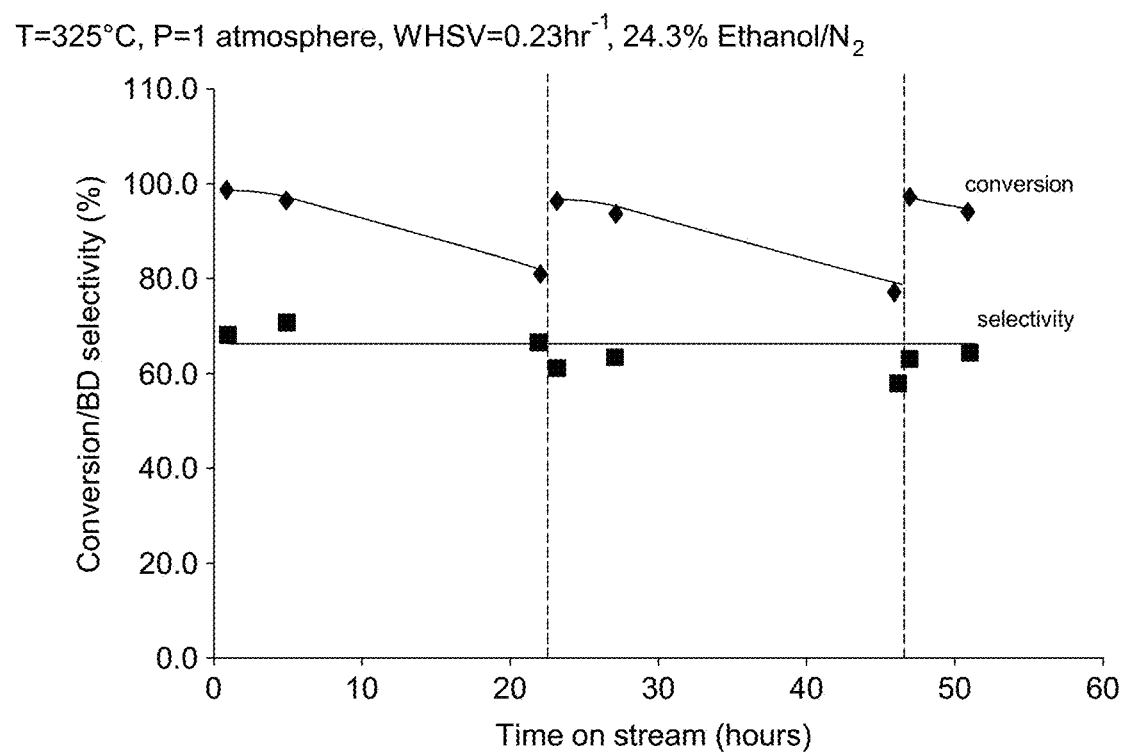
FIG. 13 shows the results of experiments performed particularly regarding to the stability and regenerability of 1Ag/4ZrO2/SiO2 (SBA-16).

FIG. 13 presents the reactivity data obtained for a series of 4Ag/yZrO$_2$/SiO$_2$ catalysts with ZrO$_2$ loading between 1 and 10 wt %. While the ZrO$_2$ loading quadrupled from 1 to 4% the conversion increases only slightly from ~79% to ~86%. In addition, when the ZrO$_2$ loading increases further to 10 wt % the conversion decreases to 82.3%. The butadiene selectivity decreases from ~71% to ~62% when the ZrO$_2$ loading increases from 1 to 10%. Similarly, the acetaldehyde selectivity decreases from about 14% to about 9% with the increase of the ZrO$_2$ loading from 1 to 10%. ZrO$_2$ is acidic and varying its loading is expected to modify the catalyst acidity.

FIG. 14 shows the effects of washing the catalyst to remove excess potassium K. As the data reflects, the reduction in K increases the conversion rate and selectivity for butadiene conversion. FIG. 15 shows the effect of hydrogen addition in increasing the stability of the catalyst. FIG. 16.

FIGS. 16-20 show the results of variations on flow rates and mixture compositions. These results demonstrate that aqueous ethanol feeds of varying concentrations could be used as source for butadiene production. Many times an ethanol feed coming out of a fermenter requires a significant amount of energy to separate ethanol from water. The present process can be used to convert ethanol to butadiene across a wide range of mixed feeds. These tests showed that mixtures such as ~30% ethanol/water mixtures (which represents something that might come directly from a standard fermenter "beer column") to be effective in this one step conversion process. While this example is shown, it is also to be understood that these examples are not limiting but are intended to show that the feedstock can be both ethanol and aqueous mixtures of ethanol. The ability to use various forms of ethanol mixtures ranging from 100 percent to 10 percent ethanol and even lower provides additional advantage in reducing the cost and complexity of converting ethanol to butadiene and provides significant economic advantage.

While various preferred embodiments of the invention are shown and described, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A method for producing 1,3-butadiene (BI)) from ethanol the method comprising:
    passing a gaseous feed containing the ethanol over a multi-functional catalyst to produce the 1,3-butadiene (BD); wherein
    the multifunctional catalyst comprises a silica support, said silica support comprises 1-10 wt % ZrO2 and has a Lewis Acid site concentration of 10-35 μmole/gram; and the multifunctional catalyst comprises silver (Ag) or copper (Cu) having a dispersion of at least 40% on the silica metal oxide support.

2. The process of claim 1 wherein the silica ZrO2 support comprises a silica selected from the group consisting of a high purity silica gel, mesoporous silica and fumed silica.

3. The process of claim 2 wherein the silica ZrO2 is a high purity SBA16.

4. The process of claim 2 wherein the silica ZrO2 is high purity SBA15.

5. The process of claim 2 wherein the silica ZrO2 is Davisil grade 646.

6. The process of claim 1 wherein hydrogen is added to the feed.

7. The process of claim 1 wherein the feed is 100% ethanol.

8. The process of claim 1 wherein the feed is a mixture containing at least 30% ethanol and includes water and wherein the process produces a yield that is at least 30% butadiene.

9. The process of claim 1 wherein the step of passing the feed containing ethanol in a gas phase is performed at a temperature between 200° C. and 375° C.

10. A process for producing 1,3-butadiene (BD) from ethanol in a single step, comprising the step of passing a feed containing ethanol in gas phase over a 1% Ag/4% $ZrO_2$/$SiO_2$-SBA-16 catalyst having a Ag dispersion of at least 40% on the $SiO_2$-SBA-16 support.

11. The process of claim 10 wherein the step of passing a feed containing ethanol is performed in operating conditions including a temperature of 325° C., pressure of 1 atm, and a flow rate of 0.23 $hr^{-1}$.

12. The process of claim 10 wherein the feed contains at east 30 percent water by weight.

* * * * *